(12) United States Patent
Chowdhury

(10) Patent No.: US 8,758,311 B2
(45) Date of Patent: Jun. 24, 2014

(54) TRANSDERMAL PATCH WITH EXTENSOR MEANS

(75) Inventor: Dewan Fazlul Hoque Chowdhury, Leicestershire (GB)

(73) Assignee: Nemaura Pharma Limited, Loughborough (GB)

( * ) Notice: Subject to any disclaimer, the term of this patent is extended or adjusted under 35 U.S.C. 154(b) by 0 days.

(21) Appl. No.: 13/195,267

(22) Filed: Aug. 1, 2011

(65) Prior Publication Data

US 2011/0288506 A1  Nov. 24, 2011

Related U.S. Application Data

(63) Continuation of application No. PCT/GB2010/000170, filed on Feb. 2, 2010.

(30) Foreign Application Priority Data

Feb. 2, 2009 (GB) .................................. 0901720.3

(51) Int. Cl.
*A61M 35/00* (2006.01)

(52) U.S. Cl.
USPC ........... 604/290; 604/289; 604/291; 600/362; 424/448; 424/449; 424/443; 424/447

(58) Field of Classification Search
USPC ......................................... 604/289, 290, 291
See application file for complete search history.

(56) References Cited

U.S. PATENT DOCUMENTS

| 4,573,996 | A | 3/1986 | Kwiatek et al. |
| 4,666,441 | A | 5/1987 | Andriola et al. |
| 4,911,707 | A | 3/1990 | Heiber et al. |

(Continued)

FOREIGN PATENT DOCUMENTS

| DE | 19849823 | 5/2000 |
| DE | 10249853 A1 | 5/2004 |

(Continued)

OTHER PUBLICATIONS

Gardeniers et al., "Silicon Micromachined Hollow Microneedles for Transdermal Liquid Transport," Journal of Microelectromechanical Systems, vol. 12, No. 6, pp. 855-862, Dec. 2003 (8 pages).
Non-final Office action dated Sep. 14, 2012, in U.S. Appl. No. 11/566,721, filed Dec. 5, 2006 (18 pages).

*Primary Examiner* — Tatyana Zalukaeva
*Assistant Examiner* — Ilya Treyger
(74) *Attorney, Agent, or Firm* — McCracken & Frank LLC (57) ABSTRACT

A transdermal product delivery patch comprises a reservoir containing a product for delivery to a patient; means for affixing the patch to the skin of the patient; and manually operable means for actuating an extensor mechanism to exert pressure on the reservoir and thereby expel the product towards the skin. The patch may be supplied with the extensor mechanism held in a strained configuration and the manually operable means may be a restraint such as a peelable layer that can be removed to allow the extensor mechanism to move using stored energy towards a rest configuration. The extensor mechanism may be a ring of resilient material that is pre-stretched radially inwards so that, upon release, it stretches the reservoir radially outwards. The patch may be supplied with the extensor mechanism in a rest configuration and the manually operable means may deform it in a pre-defined manner into a strained configuration.

17 Claims, 4 Drawing Sheets

(56) References Cited

U.S. PATENT DOCUMENTS

| | | | |
|---|---|---|---|
| 4,968,539 A | 11/1990 | Aoyagi et al. | |
| 5,234,690 A | 8/1993 | Chiang et al. | |
| 5,310,404 A | 5/1994 | Gyory et al. | |
| 5,370,635 A | 12/1994 | Strausak et al. | |
| 5,827,183 A | 10/1998 | Kurnik et al. | |
| 6,010,492 A | 1/2000 | Jacobsen et al. | |
| 6,391,643 B1 | 5/2002 | Chen et al. | |
| 2002/0002328 A1 | 1/2002 | Tamada | |
| 2003/0080085 A1 | 5/2003 | Greenberg et al. | |
| 2003/0161869 A1 | 8/2003 | Hatanaka et al. | |
| 2004/0043062 A1 | 3/2004 | Sun | |
| 2004/0219192 A1 | 11/2004 | Horstmann et al. | |
| 2007/0116752 A1 | 5/2007 | Chowdhury | |
| 2010/0016436 A1* | 1/2010 | Staniforth et al. | 514/567 |
| 2011/0178380 A1 | 7/2011 | Chowdhury | |

FOREIGN PATENT DOCUMENTS

| | | |
|---|---|---|
| EP | 0 252 459 A1 | 1/1988 |
| EP | 0 916 336 A1 | 5/1999 |
| EP | 2 015 806 B1 | 9/2009 |
| GB | 2 414 675 A | 12/2005 |
| GB | 2 434 750 A | 8/2007 |
| GB | 2 461 355 A | 1/2010 |
| WO | WO 91/03271 A1 | 3/1991 |
| WO | WO 94/09777 A1 | 5/1994 |
| WO | WO 2004/093942 A2 | 11/2004 |
| WO | WO 2005/120471 A1 | 12/2005 |
| WO | WO 2009/030351 A2 | 3/2009 |
| WO | WO 2009/050627 A1 | 4/2009 |

* cited by examiner

TRANSDERMAL PATCH WITH EXTENSOR MEANS

CROSS-REFERENCE TO RELATED PATENT APPLICATIONS

This patent application is a continuation of co-pending PCT Patent Application No. PCT/GB2010/000170, filed Feb. 2, 2010, which claims the benefit of United Kingdom Patent Application No. 0901720.3, filed Feb. 2, 2009, the entire teachings and disclosures of which are incorporated herein by reference thereto.

FIELD OF THE INVENTION

This invention relates to a patch that may be used to deliver a formulation such as a drug from a patch to the skin of a patient in a controlled manner, using an extensor mechanism to assist with expulsion of the formulation from the reservoir.

BACKGROUND OF THE INVENTION

Transdermal patches store drugs in gel reservoirs or polymer matrices and gradually release the drugs via a rate controlling membrane when applied to the skin of a patient.

In this specification, the term "drug" is used as a shorthand for any formulation that needs to be introduced into the body of a human or animal patient, whether for therapeutic or non-therapeutic (e.g. cosmetic) purposes. It may be in a form that allows it to flow under modest pressure from the reservoir to the skin, and may be a liquid, a gel, a semi-solid, a suspension of solid particulates, or a suspension of vesicles such as liposomes, niosomes, transfersomes, or elastic type vesicles.

Transdermal patches have been in use since the 1970s for the delivery of drug to a patient via the skin. This has a number of distinct clinical advantages over other means of drug delivery including enhanced patient compliance and a significant reduction in side effects due to a combination of reduced dosage requirements and by-passing of the first-pass metabolism. Patches have been developed consisting of polymer membranes into which drug is loaded, drug loaded adhesives, reservoir matrices containing saturated solutions of drug which diffuses via a rate limiting membrane and gels in which drug is incorporated. Published patent application WO 2005/120471 discloses a patch in which an extensor mechanism is actuated—typically by a microelectromechanical control—to stretch and deform the reservoir, thereby actively expelling the drug from it in a controlled manner.

Transdermal and in particular topical drug delivery has also been attained using various aqueous, gel, and suspension type formulations that are applied directly to the skin. In particular, various vesicle and nanoparticle formulations have been developed that allow a wider range of molecules to permeate the skin via the stratum corneum, which otherwise poses a formidable barrier to the ingress of foreign materials. Indeed there are numerous examples of formulations in aqueous and gel form that are approved by regulatory agencies governing the registration of medicinal products around the world. A fundamental requirement of these agencies however is to ensure the efficacy is not compromised through inadequate dosing; thus ensuring the amount of medication applied each time is controlled and preferably operator independent.

Vesicle and suspension type formulations cannot generally permeate rate controlling membranes due to their physical size and physico-chemical properties. Furthermore it would be preferred to avoid the need for a rate controlling membrane, so as to reduce the costs and timelines associated with validating the product in terms of compatibility with adhesives and the rate controlling membrane. Furthermore it would be preferable to be able to dose a specific volume of drug formulation, thus concentration of drug on to the skin, independent of operator intervention. It would also be preferable to be able to store discrete doses of the required drug in discrete packages until the point of administration, and allow it to be applied to the skin in such a manner that the formulation is not exposed to the atmosphere or prone to being disrupted in any way by the user, e.g., by being rubbed on to clothing or other objects.

BRIEF SUMMARY OF THE INVENTION

The invention provides, in an embodiment, a transdermal patch as defined in claim 1; and, in another embodiment, a method of delivering a formulation or product to the skin of a patient as defined in claim 17. Preferred, but non-essential, features of the invention are defined in the dependent claims.

In preferred embodiments of the present invention, a transdermal drug delivery patch system comprises a pouch or reservoir containing material or product to be delivered to the skin of a patient, an upper section interfaced to the reservoir layer consisting of a pre-stretched material that will relax to its original configuration upon removal of a restraint layer or mechanism, thus stretching the underlying reservoir layer in the process, and a lower section consisting of a backing material to prevent seepage of the material during storage or transit. The patch is administered to the skin by removing the lower backing layer to expose an adhesive layer surrounding the reservoir or reservoirs, and firmly bringing the adhesive layer into contact with the skin. The upper section consists of a restraining layer which when removed will cause the extensor layer (of a pre-stretched material) to revert back to its un-stretched configuration. In doing so it will cause the reservoir to stretch thus forcing the contents of the reservoir through a lower, porous, resilient membrane and bring the contents of the reservoir into contact with the skin.

It will be understood that in this specification, the words "stretch" and "stretched" do not imply an increase in the overall dimensions of a component. For example, in some embodiments of the invention, a ring-shaped component is stretched radially inwardly, while its outer diameter remains constant. The words are used with a wider meaning of resilient deformation away from a rest configuration, with associated storage of energy.

The reservoir material must be flexible to allow it to be deformed under the influence of the extensor layer, whereas the resilient membrane may be either flexible or non-flexible. When the resilient porous membrane is flexible, the pores within the membrane will stretch and thus open up under the influence of the extensor and enhance the expulsion of the contents of the reservoir towards the area in contact with the skin. In this case, the resilient membrane may be virtually non-porous in the rest position, in that the pores may be micrometers in diameter, created by a needle prick without any material removal, so that the pores close in on themselves at rest and open up only when the layer is stretched. In the case where the porous resilient membrane is not flexible, it is expected that the diameter of the pores will be sufficiently large so as not to impede the flow of material from the reservoir when the reservoir is stretched by the extensor layer upon removal of the restraint layer that keeps the extensor layer in the stretched position. It is also possible the resilient membrane is non-porous, and instead the layer fragments or disrupts or is torn open by virtue of the stretching force induced by the extensor layer.

A lower backing layer is present, adhered to the underlying skin adhesive layer to prevent any seepage of product from the reservoir, in particular where the resilient membrane is porous. This may be composed of standard backing materials made of various polymers, or cellulose. It may be hydrophobic or hydrophilic depending on the nature of the material within the reservoir, and furthermore it may consist of a layer of gel or silicone that is hydrophobic or hydrophilic, to allow the layer to provide a better seal.

The extensor layer is composed of a pre-stretched material which may be plastic or metal or any other material that has a "memory" upon deformation, such that upon release of the deforming force it will have the propensity to revert back to its natural rest state/original configuration. A spring wire for example may be bent resiliently to an angle of 90 degrees and held in that position. This is then interfaced to a flexible polymeric material to shield the metal. A restraint layer, which is a rigid non-flexible material, is then attached to the upper surface of the flexible polymer material containing the wire that is under tension. This restraint layer may be adhered using a reversible adhesive or pressure sensitive adhesive and will maintain the spring in position until the restraint layer is removed. The extensor layer is then adhered to the reservoir layer such that when the restraint layer is removed it will cause the spring to revert towards its original straight (or other) configuration, thus stretching with it the flexible film in which it is sealed, and therefore the underlying reservoir membrane (and in the case of a flexible resilient membrane, the resilient porous membrane too). It should be noted that the tension in the resilient reservoir layer will increase as the extensor layer relaxes towards its natural state. This opposition of forces may not allow the extensor layer to fully resume its original configuration before the system comes into equilibrium.

Instead of an adhesive restraint layer, the extensor layer may be restrained in the stretched position using an inextensible connection means that reversibly holds the stretched layer in the stretched position. This connection means may be for example a shape memory wire, a hook type mechanism, or some other conducting wire that will disintegrate upon receipt of a stimulus such as an electrical current or heat. This will cause the rigid connection means to be overcome by the strain exerted by the extensor layer, thus causing the extensor layer to revert to its original rest position, and in the process stretching the underlying patch reservoir and/or resilient membrane.

The extensor layer can also be produced such that there is equal outward displacement/stretching of the reservoir layer by using a disc- or ring-shaped extensor layer. The extensor layer may be restrained around the edges using a solid substrate. For example in the case of an annular extensor mechanism, a Teflon washer may be used to anchor the extensor layer at the edges.

It will be readily understood that apart from the two mechanisms described there are a number of other configurations by which stored energy in the form of a pre-stretched material may be used as an extensor mechanism. For example, the extensor layer could act on the reservoir layer in only one dimension rather than two. That dimension could be parallel to the layers or it could be perpendicular to the layers so that, for example, the extensor mechanism is effective to press down on the reservoir layer. With an extensor layer acting in one dimension, the material could be stretched in only one direction or symmetrically in two opposite directions. With an extensor layer acting in two dimensions, the extensor layer need not have circular symmetry.

Furthermore, it will be readily appreciated that, instead of being pre-stretched, such materials can be used to form an extensor layer such that on storage they are in their rest position and on application they are manually stretched a fixed distance, and locked in place such that a fixed degree of stretching of the underlying reservoir occurs. This arrangement leads to the dispensation of a finite quantity of the contents of the reservoir via the pores in a robust and reproducible manner, without operator dependence. Furthermore, the patch will allow a means of storing the product and also prevent it from being disrupted in any way after administration until the desired period of contact of the product with the skin has elapsed, after which the patch may be removed from the skin and the skin wiped clean.

The system may be composed of a single reservoir with a single extensor means or multiple reservoirs with multiple extensor means or a combination of these. A mechanical, time-controlled system could also be integrated into the patch to provide the stimulus to remove the restraint layer(s).

The adhesive may be around the periphery of the reservoir or alternatively a single reservoir layer may have the resilient membrane configured such that there are a number of compartments below the resilient membrane surrounded by a wall of adhesive or a combination of adhesive and other material. This arrangement will provide an enhanced area of contact between the skin and the patch. The restraint layer will generally form the outermost backing layer to prevent any loss of moisture from the reservoir on storage. The extensor can be arranged to cover the entire surface of the outer layer of the patch or to cover a specific area over the patch so as to expose the reservoir membrane. This may be desirable if some permeation of moisture is desired from the outer layer of the reservoir in use. In such instances the reservoir layer will be permeable to moisture, and the stretching of the reservoir will further enhance the moisture vapour permeation rate. Conversely, moisture transmission may be minimised or prevented by adhering a non-permeable membrane above the reservoir layer.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1:
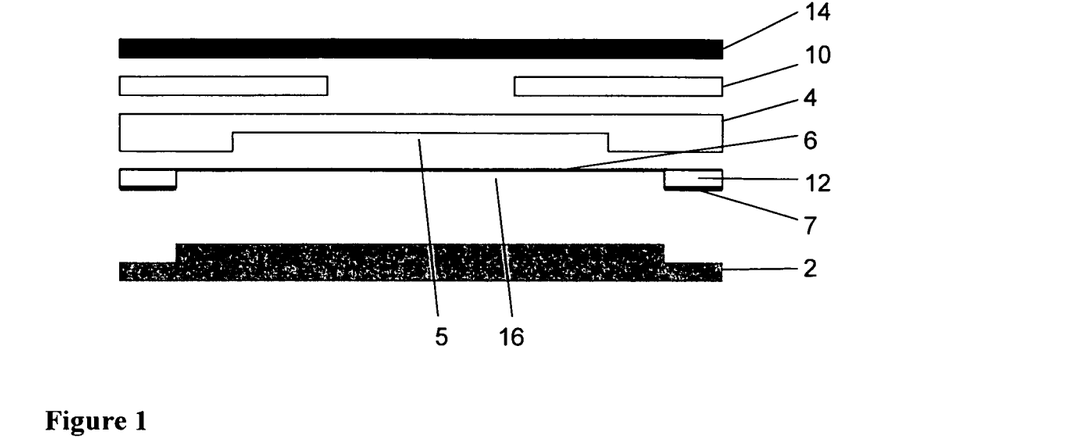
FIG. 1 is an exploded schematic cross section of a patch according to an embodiment of the invention in the rest position with the restraint layer attached to the reservoir section.
Figure 2:
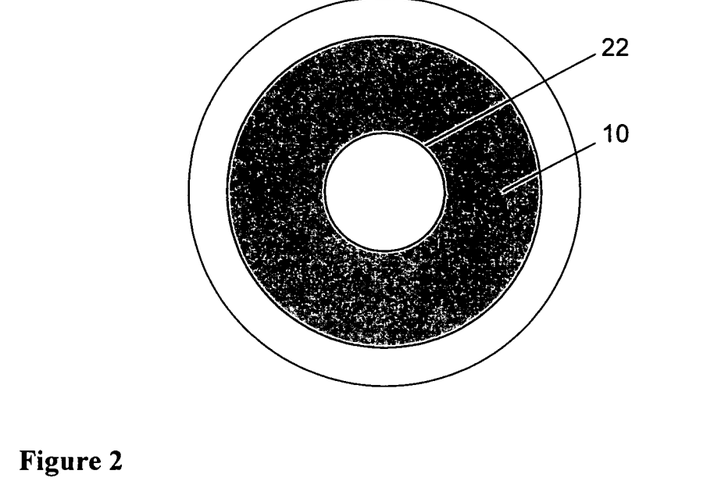
FIG. 2 illustrates a top view of the patch of FIG. 1 with a radial extensor means in the rest position (though the restraint layer is not shown here).
Figure 3:
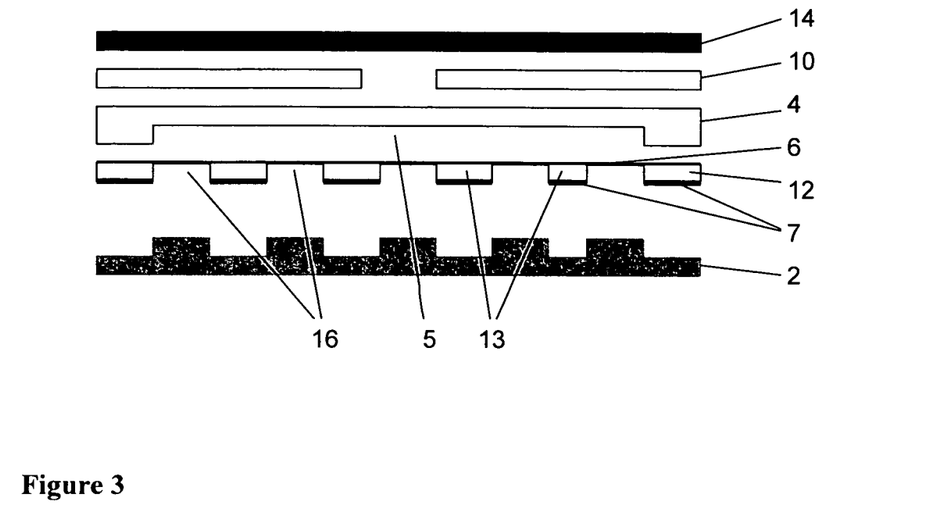
FIG. 3 is an exploded schematic cross section of an alternative patch according to the invention, indicating multiple compartments present below a single reservoir.

FIGS. 1 to 3 are schematic illustrations of transdermal patches in accordance with preferred embodiments of the present invention. A circular reservoir layer 4 comprises a central reservoir chamber 5 in which a product, typically a drug, for delivery to the patient is stored. The drug is retained in the chamber 5 by a porous resilient membrane 6, which may or may not be permeable to the drug in the rest state of the patch, as described below. Around the periphery of the resilient membrane 6, a thicker ring of material 12 provides a downwardly facing surface on which is formed a layer of adhesive 7 for adhering the patch to the skin of the patient. Inside the thicker ring 12 a compartment 16 is formed between the resilient membrane 6 and the skin of the patient, which allows the drug to collect and spread out after passing through the resilient membrane 6 and before passing into the skin. In the alternative embodiment shown in FIG. 3, there are many such compartments 16, whereby the adhesive layer 7 is formed on a network of secondary walls 13 across the whole area of the patch and not just at its periphery. The patch as stored and supplied (FIG. 1) comprises a peelable backing layer 2 to prevent the seepage of liquid from the reservoir 4 via the resilient membrane 6 during storage and to protect the adhesive layer 7 before the patch is applied to the skin.

Figure 2A:
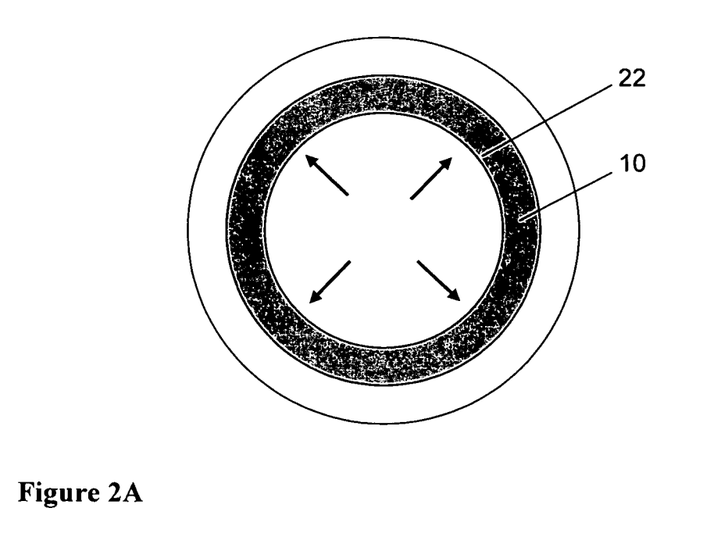
FIG. 2A illustrates a top view of the patch of FIG. 1 with the radial extensor means in the actuated position after the restraint means is removed.

Attached to an upper surface of the reservoir layer 4 is an annular extensor layer 10, best seen in FIGS. 2 and 2A, which is formed from a resilient sheet of material. During manufacture, and prior to attaching it to the reservoir layer 4, the material of the extensor layer 10 is pulled towards the centre so that the inner parts of the layer are under tension pulling them radially outwards. A restraint layer 14 is then adhered to the upper surface of the extensor layer 10 to hold it in its strained configuration during assembly, transport and storage of the patch.

Figure 1A:
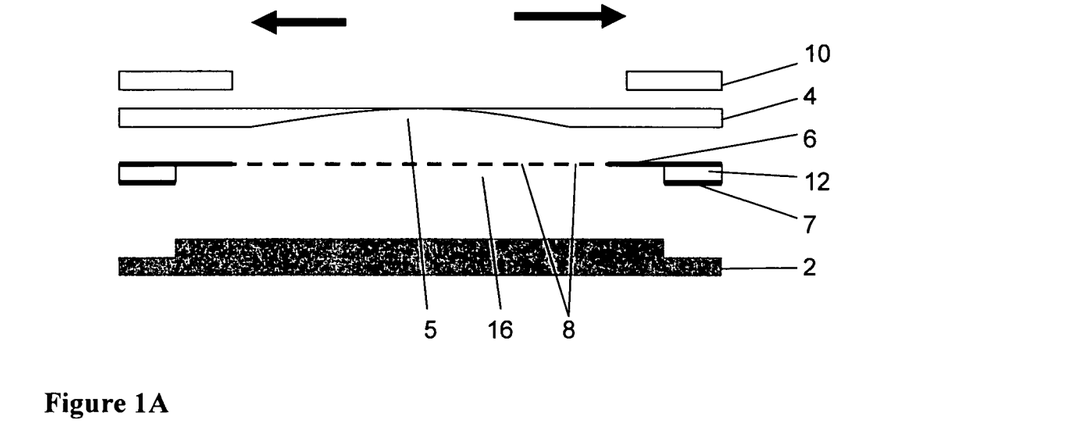
FIG. 1A is an exploded schematic cross section of the patch of FIG. 1 upon actuation of the extensor layer, i.e., once the restraint layer has been removed.

In use, the backing sheet 2 is peeled off to reveal the adhesive layer 7 and the patch is adhered to the skin of the patient. When it is desired to administer the drug stored in the reservoir 5, the restraint layer 14 is removed from the upper surface of the patch, which allows the tension in the pre-stretched extensor layer 10 to pull the inner parts of the extensor layer 10 radially outwards (FIG. 2A), thereby enlarging its central hole. The ring-shaped region of the reservoir layer 4 that is attached to the extensor layer 10 is thereby also pulled radially outwards, thereby radially stretching and thinning the reservoir chamber 5, as seen in FIG. 1A. This tends to reduce the volume of the chamber 5 and exerts pressure from the chamber walls on the contents of the reservoir to expel them through the porous membrane 6. Thus the extensor layer 10 and the reservoir layer 4 are in an "antagonistic" relationship, whereby as the extensor layer 10 relaxes towards its natural state, the reservoir layer 4 is correspondingly stretched.

The backing layer 2 may be composed of polymeric materials, cellulose, or gels based on silicone or hydrocolloids, or any other gel that will provide a hydrophobic seal for an aqueous-based product or a lipophobic seal for an oil-based product. The backing layer 2 may be a soft material that is pliable and able to conform to the contours of the resilient membrane 6, in particular where the resilient membrane 6 consists of multiple compartments 16 (FIG. 3) rather than one single compartment. Alternatively the backing layer 2 may be moulded using conventional moulding techniques to produce a template that will match the surface contour of the resilient membrane 6.

The resilient membrane 6 may be porous or non-porous and can be produced from polymers such as methacrylates, silicone, polyurethane, PTFE, and other approved pharmaceutical and medical device polymers. It may also be flexible and stretchable or it may be rigid. A rigid porous resilient membrane 6 may be used whereby the pores 8 in the membrane 6 will remain open in the rest state and will allow free passage of the contents of the reservoir chamber 5 to the skin. In this case the backing layer 2 will be designed to ensure a complete seal of all the pores 8 is obtained to prevent seepage from the reservoir 5 during storage prior to use. Generally however the seepage will not occur unless pressure is applied to the reservoir chamber 5. In this case it may be preferred to have a gel based backing layer 2 to provide higher conformance and fit to the underside of the resilient membrane 6.

A flexible porous membrane 6 may preferably be used, whereby in the rest state the pores 8 are in the closed position and on actuation of the extensor means 10 both the reservoir layer 4 and the resilient membrane 6 are stretched, thereby stretching the pores 8 within the resilient membrane 6 and opening them up as shown in FIG. 1A to allow the free passage of liquid from the reservoir chamber 5 to the skin.

Alternatively, the resilient membrane 6 may be non-porous and may be composed of a brittle material that will fragment or rupture upon extension induced by the extensor layer 10, or it may produce a tear in a non-brittle film to rupture it. The tear may be propagated along a pre-defined line that may be introduced during the production process of the membrane 6 by producing a score line which is sufficient to allow the material to rupture but not deep enough to cause the drug (not shown) to seep out from the reservoir 5 during storage.

The reservoir layer 4 may be composed from a stretchable polymeric film similar to that used for the resilient membrane 6. When it is desirable to exclude moisture from the reservoir, the film will have a low moisture transmission rate, and when the admission of moisture to the reservoir is desirable, the film will have a high moisture transmission rate, achieved primarily by altering the hydrophobicity/hydrophilicity and/or the relative porosity of the material. The reservoir layer 4 and resilient membrane 6 may be attached together using a pressure sensitive adhesive or by heat sealing, or a combination of the two. The patch may consist of one or more reservoir chambers 5, and the respective reservoirs 5 may be associated with their own extensor means 10, or be configured in a way that will allow multiple reservoirs 5 to be actuated by a single extensor means 10.

The extensor layer 10 acts to extend the underlying reservoir layer 4 and optionally also the resilient membrane 6. It may also be integrated with the reservoir 4 and resilient membrane 6 in such way that it also causes stretching of the underlying skin. In the latter case the body of the peripheral section 12 of the reservoir/resilient membrane 6 that is attached to the skin will be wider so as to allow for the stretching of the skin without allowing the patch to lose skin adhesion. Alternatively the tensile strength of the section 12 of the patch in contact with the skin may be altered such that the extensor forces induced by the extensor layer 10 are high enough to provide the requisite forces on the reservoir layer 4 and resilient membrane 6, yet modulated above the skin such that the forces are sufficient to cause slight stretching of the skin, but not cause loss of the adhesion to the skin. The stretching of the skin has most significance where it may be desirable to deliver medicaments to the follicles and skin appendages, in particular drugs loaded in particles or vesicles. Furthermore, extension of the pores of the skin would augment iontophoretic drug delivery, since in iontophoresis most of the enhanced permeation is attributable to drug being forced through the skin pores and follicular pathway.

The extensor layer 10 could be integrated into any one side of the patch or the entire surface of the patch, and it may also be integrated such that it is directly interfaced to the resilient membrane 6 or the reservoir layer 4. It could for example be integrated with the resilient membrane 6 by having the resilient membrane 6 protrude on any one side of the extensor layer 10 or around its entire periphery, beyond the reservoir chamber 5 itself, thus the extensor force being exerted directly on the resilient membrane 6 and not the reservoir chamber 5. The extensor mechanism 10 may be composed of any resilient material that can be stretched and then held in position using a restraint means 14, such as a non-flexing material. A spring wire, or a rubber material or a polymeric material such as PTFE or other that has been shaped to allow a degree of bend such that it retains memory of its original shape and springs back to it once the restraint is removed. The material could be a rubber-like film such as latex or polyurethane. Alternatively the spring or plastic moulded materials may be integrated into a resilient and robust stretchable polymer film to form an 'extensor layer' 10, which protects both them and the user. This also aids with the final manufacturing step whereby the extensor layer 10 can be produced separately and heat sealed or adhered onto the top of the patch, after the reservoir 5 has been filled and the resilient membrane, skin adhesive and backing layer have already been attached. The outer surface of the extensor layer 10 and/or the reservoir layer 4 that is exposed to the environment may consist of foam backing to provide a soft feel on adhering the patch to the skin.

The restraint layer 14 is a material that will withstand the forces exerted upon it by the pre-stretched underlying material 10. This may be metal-based, cellulose, or polymer-based, and it may be either sealed to the extensor layer 10 using an adhesive, allowing it to be easily removed without leaving any residue of adhesive on the surface of the patch, or alternatively it may be welded or heat sealed to an upper part of the patch in a manner that allows the extensor layer 10 to be kept in the restrained position and not buckle throughout its shelf life and during application of the patch to the skin, until it is desired for the extensor mechanism 10 to be actuated. There may be a tab of some form (not shown) to allow the restraint layer 14 to be easily and firmly gripped and readily peeled off/removed from the extensor layer 10, without causing the patch to delaminate either from its sub-components or from the skin.

The annular extensor layer would be produced by taking a sheet of the material, e.g., a rubber-like polymer and restraining this around its perimeter/circumference, e.g., by pressing/clamping it between an upper and lower solid ring. Below the centre of the polymer film an opening (of a given diameter) is present via which a vacuum sucks in the polymer thus stretching it towards the centre. The restraint layer is subsequently adhered over the entire surface of this pre-stretched polymer extensor layer using an adhesive that is reversible (i.e., the restraint layer can be easily peeled off). A die is then used to cut out a middle section and in doing so removing the excess stretched part of the polymer sucked in by the vacuum. The resulting ring of pre-stretched material will constitute a radial extensor means/layer and can be attached to the reservoir layer simply by sandwiching the sections together using adhesive, with the restraint layer being the outermost layer of the patch.

Figure 4:
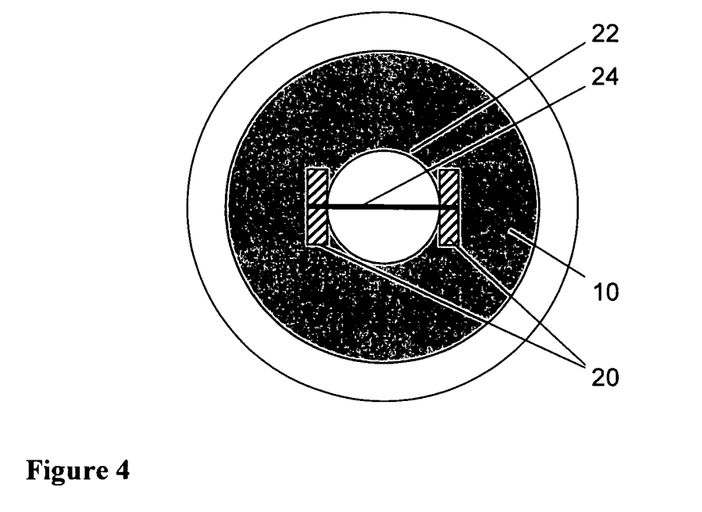
FIG. 4 is a top view of the patch, similar to FIG. 2 but with an alternative restraint mechanism, in a strained configuration.
Figure 4A:
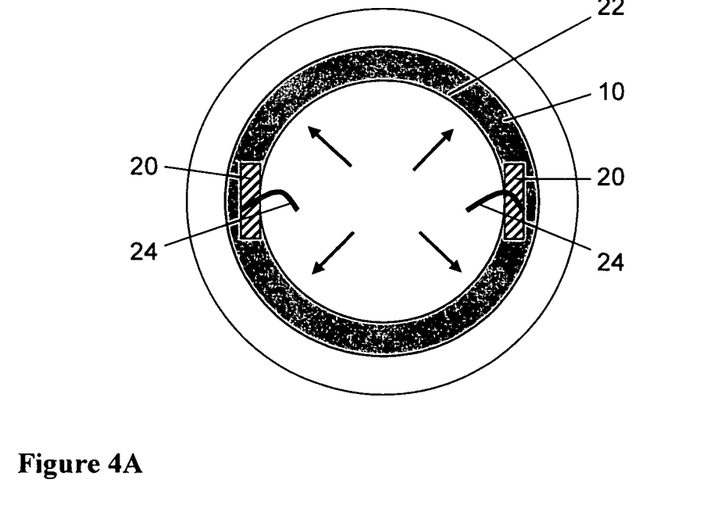
FIG. 4A is a top view of the patch of FIG. 4 after the restraint means is removed.

FIGS. 4 and 4A show an alternative form of restraint mechanism for an annular extensor mechanism 10 similar to that in FIGS. 2 and 2A. Anchor points 20 near the inner edge 22 of the extensor layer are joined together by a connector 24 such as fuse wire that is substantially rigid (at least while under tension). This holds the extensor layer 10 in its stretched configuration. On application of heat to the connector 24, for example by passing an electric current through it, the connector 24 disintegrates and can no longer resist the tensile forces in the extensor layer 10. The extensor layer therefore relaxes radially outwards towards its rest position, as shown in FIG. 4A, in the process stretching the reservoir layer below.

In another embodiment of the patch (not illustrated), the extensor mechanism uses a compressed open-cell foam to store energy. During manufacture, the foam is formed into a suitable configuration in a pouch that is impermeable to air. Air is evacuated from the pouch so that the resilient foam is compressed by ambient atmospheric pressure. In order to actuate the extensor, the pouch is punctured to allow air to flow back into the cells of the foam and expand it to its natural size and shape, thereby creating the desired strain on the neighbouring reservoir. One way of puncturing the pouch is to pass an electrical current through a suitably formed element of shape memory metal, thereby causing a transition of the element to a different configuration in which it applies a sharp point to the pouch.

In another embodiment of the patch (not illustrated), electrodes may be provided in the compartment(s) 16 adjacent to but not in direct contact with the skin, for example silver, silver/silver-chloride, platinum or carbon-based electrodes. These may then be interfaced to a power supply and control module such that the drug may be delivered into the skin via active facilitation using an electrical current, such as in iontophoresis, rather than just by passive diffusion under pressure from the reservoir.

In another embodiment of the patch (not illustrated) the extensor layer 10 may not require any pre-stretched component or indeed a source of stored energy, and instead the stretching of the reservoir 4 and/or extensor layer 10 may be manually instigated by for example having two plates that are situated at two ends of the patch and are manually pushed towards each other by use of grip points and which then lock into each other either permanently or reversibly (rather like the clips on a suitcase belt). This would achieve the same desired outcome of ensuring that a pre-determined strain is exerted on the extensor layer 10 and therefore a pre-determined dose is released from the reservoir 5 to the skin via the resilient membrane 6. However, the preferred embodiment is that described above, whereby removal of the restraint layer 14 leads to the reservoirs 5 being automatically activated to dispense the dose, as that is completely operator-independent, whereas this latter embodiment requires an element of operator co-ordination, and has the potential to cause the patch to come off the skin if the pressure is not applied evenly to the stretching mechanism.

Although the invention has been described in the context of the application of the delivery of formulations for therapeutic or cosmetic applications to the skin of a patient, which may be human or animal, it will be appreciated that the applications are broader in scope. This type of patch may be used for any purpose whereby a defined volume of fluid is to be dispensed from the reservoir(s) of the patch to a second body or receptacle, where it is desired to be exposed to that second body for a period of time. This may include for example the release of a chemical on to a second material so as to induce oxidation and lead to an exothermic reaction to increase the temperature of an object, or to use the increased temperature as a stimulus to cause an actuation of a device, for example a device that contains a shape memory alloy, whereby the shape memory alloy will undergo a change in shape in response to an increase in temperature.

It could also be used to irrigate wounds and to treat wounds by having multiple reservoirs covering a single large extensor layer. In such an embodiment, a reservoir can be actuated to release all the fluid contained within it to cover the entire area covered by the resilient membrane, which would be designed to cover a wound. At a given point in time the fluid can be removed from the surface of the wound by inserting a needle between the skin and resilient membrane. A second reservoir can then be activated for fresh fluid to be dispensed to the wound. This may be repeated a number of times, depending on the needs of the wound (according to which the number of reservoirs would be designed). The key issue this will address is that of treating a wound without having to open up the dressing to remove fluids that build up during the wound healing process, thus maintaining the aseptic integrity during wound management, thereby enhancing the speed of recovery, and preventing subsequent infections during the healing process. An alternative to inserting a needle would be to have a conduit linking the space between the skin and the resilient membrane to the outside of the patch (with a venting valve) to allow a syringe to be connected, which may also be designed to ensure a specific volume of fluid is withdrawn each time, and the would could also be irrigated using this mechanism by adding saline or antiseptic solutions via the conduit and the actuating a reservoir to release a pre-defined volume of drug/therapeutic agent if desired.

The patch could also be used for non-medical applications such as managing plant disease, e.g., localised infection/damage that requires liquid product to be in contact with the area over a prolonged period. In each application an adhesive to secure the patch would be selected based on the substrate to which it is intended to be applied.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A transdermal patch comprising:
   a reservoir containing a product for delivery to a patient;
   an extensor mechanism comprising a resilient element;
   means for affixing the patch to the skin of the patient; and
   manually operable means for actuating the extensor mechanism while the patch is affixed to the skin to expel the product towards the skin of the patient;
   wherein the extensor mechanism in a strained configuration prior to use of the patch, the resilient element being stretched in the strained configuration of the extensor mechanism; and
   wherein the manually operable means is a restraint that can be removed on use of the patch to allow the extensor mechanism to move using stored energy from the strained configuration towards a rest configuration.

2. A transdermal patch according to claim 1, wherein the manually operable means is effective to exert pressure on the reservoir.

3. A transdermal patch according to claim 1, wherein the manually operable means is effective to move parts of the extensor mechanism through a predetermined distance.

4. A transdermal patch according to claim 1, wherein the restraint is a peelable layer.

5. A transdermal patch according to claim 1, wherein the restraint is a connector that can be broken by the manually operable means.

6. A transdermal patch according to claim 5, wherein the restraint is a wire and wherein the manually operable means is effective to weaken the wire by passing an electric current through it.

7. A transdermal patch according to claim 1, wherein the resilient element is a disc or ring that is stretched radially inwardly in the strained configuration.

8. A transdermal patch according to claim 1, wherein the reservoir is formed in a resilient layer of the patch; and wherein the actuation of the extensor mechanism exerts pressure on the reservoir by stretching the resilient layer to cause thinning of the reservoir.

9. A transdermal patch according to claim 8, further comprising a resilient, porous membrane between the reservoir and the skin of the patient; wherein the actuation of the extensor mechanism is effective to stretch the resilient porous membrane and thereby increase its permeability to the product.

10. A transdermal patch according to claim 1, further comprising a wall around the perimeter of the patch, the wall having an adhesive layer for adhering the patch to the skin of the patient, the wall thereby defining a compartment between the patch and the skin.

11. A transdermal patch according to claim 10, further comprising secondary walls within the perimeter of the patch, the secondary walls defining multiple compartments between the patch and the skin.

12. A transdermal patch comprising:
a reservoir containing a product for delivery to a patient;
an extensor mechanism;
means for affixing the patch to the skin of the patient; and
manually operable means for actuating the extensor mechanism while the patch is affixed to the skin to expel the product towards the skin of the patient;
wherein the extensor mechanism is in a rest configuration prior to use of the patch and the manually operable means is effective to deform the extensor mechanism in a predefined manner from the rest configuration into a strained configuration; and
wherein the manually operable means comprises tabs attached at two points on the extensor mechanism that can be manually drawn together, the patch further comprising means for latching the two tabs together to hold the extensor mechanism in its strained configuration.

13. A method of delivering a product to the skin of a patient, comprising:
affixing a transdermal patch to the skin of the patient, the patch comprising a reservoir containing the product and an extensor mechanism, the extensor mechanism comprising a resilient element, the extensor mechanism being held in a strained configuration in which the resilient element is stretched; and
after affixing the patch to the skin, manually actuating the extensor mechanism in the patch to expel the product towards the skin, wherein manually actuating the extensor mechanism comprises removing a restraint to allow the extensor mechanism to move using stored energy from the strained configuration towards a rest configuration.

14. A method according to claim 13, wherein manually actuating the extensor mechanism is effective to exert pressure on the reservoir.

15. A method according to claim 14, wherein manually actuating the extensor mechanism comprises moving parts of the extensor mechanism through a predetermined distance.

16. A method according to claim 13, wherein removing the restraint comprises peeling a layer off the patch.

17. A method of delivering a product to the skin of a patient, comprising:
affixing a transdermal patch to the skin of the patient, the patch comprising a reservoir containing the product and an extensor mechanism, the extensor mechanism being in a rest configuration; and
after affixing the patch to the skin, manually actuating the extensor mechanism in the patch to expel the product towards the skin, wherein manually actuating the extensor mechanism comprises deforming the extensor mechanism in a predefined manner into a strained configuration by drawing towards one another tabs that are attached at two points on the extensor mechanism and latching the two tabs together to hold the extensor mechanism in its strained configuration.

* * * * *